United States Patent
Bürk (10) Patent No.: US 11,000,294 B2
(45) Date of Patent: May 11, 2021

(54) SURGICAL GRIP WITH AN INTERNAL AND SPRING-BIASED ROTATION SECURING UNIT

(71) Applicant: Aesculap AG, Tuttlingen (DE)

(72) Inventor: André Bürk, Villingen-Schwenningen (DE)

(73) Assignee: AESCULAP AG, Tuttlingen (DE)

( * ) Notice: Subject to any disclaimer, the term of this patent is extended or adjusted under 35 U.S.C. 154(b) by 504 days.

(21) Appl. No.: 15/740,058

(22) PCT Filed: Jun. 16, 2016

(86) PCT No.: PCT/EP2016/063825
§ 371 (c)(1),
(2) Date: Dec. 27, 2017

(87) PCT Pub. No.: WO2017/001202
PCT Pub. Date: Jan. 5, 2017

(65) Prior Publication Data
US 2018/0185035 A1    Jul. 5, 2018

(30) Foreign Application Priority Data
Jun. 29, 2015 (DE) .................. 10 2015 110 415.6

(51) Int. Cl.
*A61B 17/16* (2006.01)
*A61B 17/32* (2006.01)
(Continued)

(52) U.S. Cl.
CPC ........ *A61B 17/1633* (2013.01); *A61B 17/162* (2013.01); *A61B 17/32002* (2013.01);
(Continued)

(58) Field of Classification Search
CPC ............ A61B 17/1622; A61B 17/1624; A61B 17/1659; A61B 17/162; A61B 17/1633;
(Continued)

(56) References Cited

U.S. PATENT DOCUMENTS 5,823,774 A     10/1998 Abbott et al.
5,888,200 A  *   3/1999 Walen ................ A61B 17/1622
                                                         606/167
(Continued)

FOREIGN PATENT DOCUMENTS

DE          10311455 B3     9/2004
DE       102013111194 A1    4/2015
(Continued)

OTHER PUBLICATIONS

Russian Office Action for Russian Application No. 2018103058/14(004411), dated Oct. 17, 2019, with translation, 20 pages.
(Continued)

*Primary Examiner* — Marcela I. Shirsat (57) ABSTRACT

A surgical grip for receiving a handpiece shaft for conjoint rotation therewith and/or for receiving a medical tool in such a way as to transmit torque, includes a carrier sleeve on which at least one coupling component provided for coupling the handpiece shaft is attached such that the at least one coupling component can be brought to a coupled position and to an uncoupled position in the operating state, wherein the at least one coupling component can be brought into contact with an activation unit which is arranged between the carrier sleeve and an outer actuation sleeve, wherein a rotation securing unit present inside the actuation sleeve acts on the activation unit in a spring-biased manner in the operating state such that the activation unit is held secure against rotation relative to the carrier sleeve.

6 Claims, 9 Drawing Sheets

(51) Int. Cl.
  *B23B 31/107*    (2006.01)
  *B23B 31/20*     (2006.01)
  *A61B 17/00*     (2006.01)
  *A61B 90/00*     (2016.01)
  *A61C 17/02*     (2006.01)
  *A61C 1/14*      (2006.01)
  *B23B 51/12*     (2006.01)

(52) U.S. Cl.
  CPC ........ *B23B 31/1072* (2013.01); *B23B 31/201* (2013.01); *A61B 17/1622* (2013.01); *A61B 2017/0046* (2013.01); *A61B 2017/00477* (2013.01); *A61B 2090/0813* (2016.02); *A61C 1/144* (2013.01); *A61C 17/0202* (2013.01); *B23B 31/107* (2013.01); *B23B 31/1071* (2013.01); *B23B 51/126* (2013.01)

(58) Field of Classification Search
  CPC ...... A61B 17/32002; A61B 2017/0046; A61B 2017/00477; A61B 2090/0813; A61B 17/1615; A61B 2017/00464; B23B 31/1074; B23B 31/201; B23B 31/107; B23B 31/1071; B23B 51/126; A61C 17/0202; A61C 1/07; A61C 1/141; A61C 1/144; A61C 1/08; A61C 1/12; A61C 1/10; A61C 1/147; A61C 3/03; A61C 3/02

USPC .......... 606/80, 167; 433/51–52, 84, 86, 103, 433/114, 128–129
  See application file for complete search history.

(56) References Cited

U.S. PATENT DOCUMENTS

| | | | |
|---|---|---|---|
| 5,928,241 | A  | 7/1999  | Menut et al. |
| 5,989,257 | A  | 11/1999 | Tidwell et al. |
| 6,209,886 | B1 | 4/2001  | Estes et al. |
| 2006/0053974 | A1 | 3/2006  | Blust et al. |
| 2008/0287739 | A1 | 11/2008 | Smith et al. |

FOREIGN PATENT DOCUMENTS

| | | |
|---|---|---|
| EP | 0837749 B1    | 7/2002 |
| EP | 1598023 A2    | 11/2005 |
| WO | 1997000149 A1 | 1/1997 |

OTHER PUBLICATIONS

German Search Report for German Application No. 10 2015 110 415.6, with translation, dated Apr. 13, 2016—9 Pages.
International Search Report and Written Opinion for International Application No. PCT/EP2016/063825, dated Aug. 1, 2016—10 Pages.

\* cited by examiner

SURGICAL GRIP WITH AN INTERNAL AND SPRING-BIASED ROTATION SECURING UNIT

RELATED APPLICATION(S)

This application is the United States national phase entry of International Application No. PCT/EP2016/063825, filed Jun. 16, 2016, which is related to and claims the benefit of priority of German Application No. 10 2015 110 415.6, filed Jun. 29, 2015. The contents of International Application No. PCT/EP2016/063825 and German Application No. 10 2015 110 415.6 are incorporated by reference herein in their entireties.

FIELD

The invention relates to a surgical grip for receiving a handpiece shaft for conjoint rotation therewith and/or for receiving a medical tool in such way as to transmit torque, comprising a carrier sleeve to which at least one coupling component provided for coupling the handpiece shaft, such as at least one ball, one cylinder or one cone, is attached so that the at least one coupling component can be brought to an coupled position and to an uncoupled position in the operating state, wherein the at least one coupling component can be brought into contact with an activation unit arranged between the carrier sleeve and an outer actuation sleeve.

BACKGROUND

From the state of the art, e.g. EP 1 598 023 B1, a medical handpiece is known already. It comprises a cutting tool including a flexible shaft and a drill provided at the distal end of the shaft for cutting an area concerned, a tubular sleeve for receiving the cutting tool therein and a handpiece member for releasably holding the proximal end of the cutting tool and transmitting drive force from a drive source to the cutting tool, the sleeve and the cutting tool being rendered flexible for a particular area, wherein the sleeve is adapted to be plastically deformed while the shaft of the cutting tool is elastically deformed. It is emphasized as, a special feature that the medical handpiece includes a plurality of bearings arranged in the sleeve, includes first interposed members which are tubular and flexible and are arranged proximally relative to, distally relative to and between the bearings, and that second interposed members are provided which are tubular and flexible and are arranged inside the first interposed members, with the second interposed members incorporating the shaft of the cutting tool.

Surgical grips thus include actuation elements which may as well be sleeve-shaped. However, such actuation sleeves have to be secured so that no inadvertent disassembly can take place. Securing is also carried out by an axially displaceable actuation sleeve, wherein parts adjacent to the outside of the actuation sleeve then may exhibit a space that allows pinching of an OP glove. This is intended to be avoided, however. In the ideal case, no visible external changes are to be made to the actuation sleeve. Nevertheless, damage-fee disassembly of the actuation sleeve is to remain possible.

The known solutions by means of an externally visible screw of a nut screwed onto the carrier sleeve are not sufficient in terms of esthetics and hygiene. So, OP gloves may be pinched, for example, and sterilization is difficult to obtain. Even alternatively imagined internal circlips do not help to achieve easy disassembly. Frequently, even disassembly bores entailing an additional penetration point for contaminations will have to be introduced, which negatively affects the cleaning capability. It has to be further complained that a puncture restricts the stability of the shaft along which the actuation sleeve is intended to move.

The solution of an externally arranged screw or nut does not only considerably influence the appearance but also negatively affects the safety. If the screw or the nut will become unscrewed, the safety of the actuation sleeve is no longer guaranteed. The screw head further offers a contact surface for contaminations and thus is more difficult and, resp., more complicated to clean.

SUMMARY

It is the object of the present invention to eliminate or at least to alleviate the drawbacks from the state of the art. In particular, pinching of an OP glove is to be rendered impossible and safe but damage-free disassembly is to be facilitated. Further, the sterilizing capability is to be enhanced.

Secondary aspects relate to the fact that axial and radial securing of the actuation sleeve is to be enabled between two end positions, torque transmission from the actuation sleeve to an application member is to be enabled, actuation of a closing sleeve for the shaft coupling is to be facilitated, actuation of a push rod for a detent mechanism is to be possible failure-free, securing against undesired automatic disassembly of the actuation sleeve during use, for example in the case of vibrations, impacts and/or jolts, is to be held and a connecting technology is to be selected which ensures simple and destruction-free assembly and disassembly.

According, to the invention, this object is achieved in a generic surgical grip by the fact that a rotation securing unit present inside the actuation sleeve acts on the activation unit in a spring-biased manner in the operating state such that the activation unit is held secure against rotation relative to the carrier sleeve.

Advantageous embodiments will be described in detail as follows.

It is of advantage when the actuation sleeve can be displaced in a disassembling state different from the operating state to a position enabling rotation of the activation unit. In this way, although on the one hand trouble-free operation is continuously enabled, also disassembly is ensured, for example in the case of maintenance/service of the surgical grip, if, the disassembling state is deliberately intended, however. For efficient use of the surgical grip in the operating state it is advantageous when the activation unit includes a stop sleeve and a closing sleeve separate therefrom.

Accordingly, it is of advantage when the closing sleeve has such inner contour that during axial displacement of the closing sleeve the coupling component is automatically displaced between the coupled and, the uncoupled position. Safe coupling and uncoupling of the handpiece shaft is ensured in this way.

It is useful when the stop sleeve is attached to the actuation sleeve in an axially and/or radially fixed manner. In this way, an activating motion can be transmitted from the actuation sleeve to the stop sleeve without any loss.

An advantageous configuration is also characterized in that the actuation sleeve includes a shoulder or a bottom designed for catching the closing sleeve after covering an axial dead travel. So, first an intended axial displacement of the actuation sleeve has to be effectuated before the handpiece shaft is uncoupled. Accordingly, the operating safety of the surgical grip is increased.

It is further mentioned in this context that the invention also relates to the surgical grip with the coupled handpiece shaft and/or the coupled tool, of course.

It is advantageous when the stop sleeve is connected to the actuation sleeve in an axially fixed manner and is radially adjustable at two, three or more positions.

In order to prevent the rotation securing unit from performing any rotations on its own it is of advantage when said unit is guided on the carrier sleeve for conjoint rotation therewith but in an axially movable, manner. Intended activation and deactivation of the disassembling state and, resp., enabling the disassembling state is facilitated in this way.

It is further advantageous when the rotation securing unit includes one, two, three or more guiding arms, with the guiding arm or guiding arms being supported in a guiding groove and, resp., in each guiding groove or in a guiding passage and, resp., in each guiding passage, for example on the outside of the carrier sleeve preferably free from play. This helps to facilitate the assembly and to improve the function of the grip.

It is of advantage when a plurality of coupling components of the ball type can be brought into a coupled position protruding through each of the through-openings of the carrier sleeve by axially moving the closing sleeve.

An advantageous configuration is also characterized in that the rotation securing unit is forced into form closure with the activation unit via an anti-rotation spring/rotation securing spring bearing against a portion or component fixed to the carrier sleeve. The rotation securing unit then always holds such position that inadvertent and inherently intended rotation of the activation unit, especially of the stop sleeve, is prevented. Only after intended displacement of the rotation securing unit in the proximal direction, i.e. away from the activation unit and especially from the stop sleeve, is an intended rotation of the stop sleeve enabled for disassembly.

It is useful when front-face rotation securing tabs of the rotation securing unit pointing approximately in the axial direction engage in preferably diametrically opposed front-face rotation securing recesses, which e.g. point in the axial direction, in the operating state. Then proper cohesion of the two individual components is achieved with detachability being ensured as well.

It is of advantage when the rotation securing unit includes a transmission sleeve having two opposite guiding arms and comprises a support ring positively and/or non-positively attached to the transmission sleeve on which the anti-rotation spring is supported.

For efficient interaction of the individual components it is also advantageous when the support ring includes at least one, preferably inwardly protruding, supporting lug, further preferred plural supporting lugs, positively engaging in a recess of the transmission sleeve. When plural supporting lugs are provided, also plural recesses are provided, of course, with each supporting lug positively engaging in a respective recess. It has turned out to be useful to form the supporting lugs and the recesses evenly spread when viewed over the periphery.

In order to enable operationally safe coupling of the individual components it is of advantage when the recess is in the form of a bayonet lock and preferably has a detent24 area for receiving the supporting lugs.

The assembly is enhanced, when the anti-rotation spring is arranged substantially outside the transmission sleeve. Also, service can be implemented in a quicker, cheaper and more efficient manner.

It is advantageous when at least one stop pin disposed in a guiding groove of the stop sleeve is inserted in the carrier sleeve. Of course, it is advantageous to employ plural stop pins each being present in a guiding groove. In this case, too, equal spreading when viewed over the periphery has turned out to be advantageous and to counteract overturning moments.

It is advantageous when a release groove provided inside of the stop sleeve and being aligned in the circumferential direction is present on the inside of the stop sleeve.

It is of advantage when the release groove and/or an ejection groove is/are adapted to the stop pin and/or to each other as to position and geometry so that the stop pin immerses into the release groove upon rotation with the stop sleeve and, in the ease of subsequent axial displacement of the stop sleeve, bends into an ejection groove opening into the release groove so as to release the stop sleeve.

When the release groove is disposed approximately/exactly centrally between the end positions of the stop sleeve during axial displacement thereof in the operating state, an operating person first has to intentionally displace the actuation sleeve and further intentionally search the release groove to be found between the end positions in order to then carry out a disassembly which is unwanted in the operating state, however. In this way, the protection against disassembly during (normal) operation is considerably increased.

Moreover, it is of advantage when the release groove opens into the guiding groove in the center thereof.

It has turned out to be advantageous when in the operating state the support ring is in contact with the transmission sleeve and the latter in turn contacts the stop sleeve. Exact actuation is possible in this case.

For a rattle-free operation it is of advantage when the stop sleeve is mounted (only) non-positively and/or positively to the actuation sleeve or is mounted (only) by material adhesion. Then the individual parts are also prevented from being inadvertently rotated against each other.

It is of advantage when on the outside of the stop sleeve mounting tabs, for example in the way of clip springs, are provided and/or detent lugs engaging in detent contours on the inside of the actuation sleeve which non-positively and/or positively receive said detent lugs, in the first case, aligning of the actuation sleeve relative to the further inwardly located parts is enabled and is then finalized e.g. by material adhesion of the stop sleeve to the actuation sleeve, whereas, in the second case, even later alignment of the actuation sleeve relative to the remaining handpiece can be achieved by the operating surgeon. This may be especially advantageous when the actuation sleeve takes a non-symmetric shape, for example includes recessed grips.

An advantageous embodiment is also characterized in that the rotation securing unit comprises a latching web, for example having notches on the outer surface thereof, which is arranged to be accessible outside of the grip. The notches then may be utilized, for example, to facilitate the action of a tool and to facilitate disassembly during service.

An advantageous embodiment is also characterized in that the rotation securing unit includes one, two, three or more guiding groove(s) engaged in guiding elements which are connected to the carrier sleeve, and/or the stop sleeve has one or more radial release groove(s) opening into the guiding groove(s) which in turn open(s) into one or more release groove(s).

In other words, the actuation sleeve is secured by internal stop pins in the axial direction and in the radial direction. In the axial direction, movement of the actuation sleeve is possible between the locking position and the unlocking position. Locking works automatically via a spring. Unlocking only works when the latching web connected in series with the actuation sleeve is released and a user pushes the actuation sleeve back against the spring force. In the radial direction, the actuation sleeve is secured against rotation over the entire distance.

In its interior the actuation sleeve has a specific stop sleeve including the detent contour for the pins. In combination with a transmission sleeve engaging in the stop sleeve, simple assembly and damage-free disassembly are possible. The actuation sleeve can be continuously adjusted as to its radial position relative to the stop sleeve and thus relative to the entire application member. With an angled application member, this enables the holding position to be exactly aligned. After adjusting the position, the actuation sleeve is disassembled and is tightly connected to the stop sleeve, for example by, means of laser welding. The individual parts of the surgical grip are preferably made from a steel alloy, e.g. from a stainless steel alloy. Spring elements integrated in the stop sleeve are fixing them in the actuation sleeve until the final fixation.

In a special embodiment, the stop sleeve is connected to the actuation sleeve via a detent contour. No tight fixation is performed. This enables the user to radially adjust the actuation sleeve so as to set further holding positions of the application member.

It is especially worth mentioning that the stop sleeve integrated in the actuation sleeve has an unlocking position between the two end positions. By releasing a transmission sleeve, the actuation sleeve may be easily assembled and disassembled. In addition, the stop sleeve permits continuous adjustment of the actuation sleeve during assembly. In another configuration, a locking adjustment of the actuation sleeve by the user is possible.

Pinching of gloves is excluded as external stops are renounced. As a result, the actuation sleeve is easy to purify, because its outer contour is designed to be in one piece. This allows for an unrestricted design of the outer contour in accordance with an advantageous design configuration.

Hence an axially movable actuation sleeve secured by internal stops is presented. The actuation sleeve may be easily mounted, be adjusted as to its radial orientation and be disassembled free from damage, if required.

BRIEF DESCRIPTION OF THE DRAWING FIGURES

Hereinafter, the invention shall be illustrated in detail by way of a drawing, wherein.

The figures are merely schematic and only serve for the comprehension of the invention. Like elements are provided with like reference numerals. Features of die individual embodiments may be exchanged for each other.

DETAILED DESCRIPTION

Figure 1:
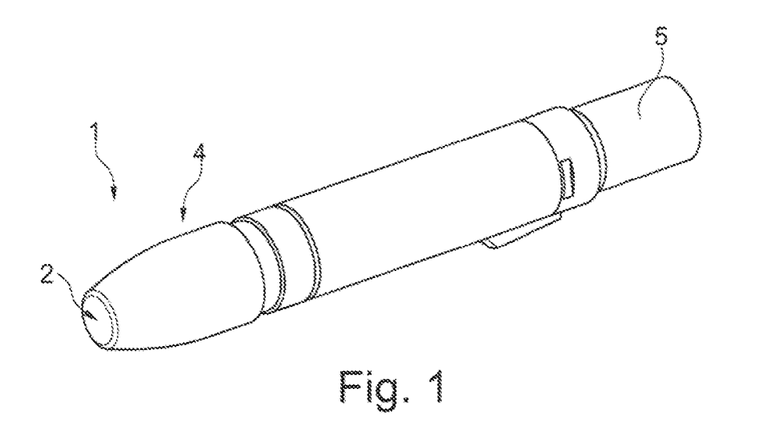
FIG. 1 shows a first embodiment of a surgical grip with an internal stop according to the invention in a perspective view.

FIG. 1 shows a first embodiment of a surgical grip 1 according to the invention. The surgical grip 1 may also be referred to as handpiece. It is provided for receiving a band piece shaft (not shown) and for receiving a medical tool such as a milling cutter (not shown). In the interior, it includes a carrier sleeve 2 which is such a central component relative to which possible movable elements are movable. Surrounding the carrier sleeve, an activation unit 3 clearly visible in FIG. 5 is provided.

Figure 2:
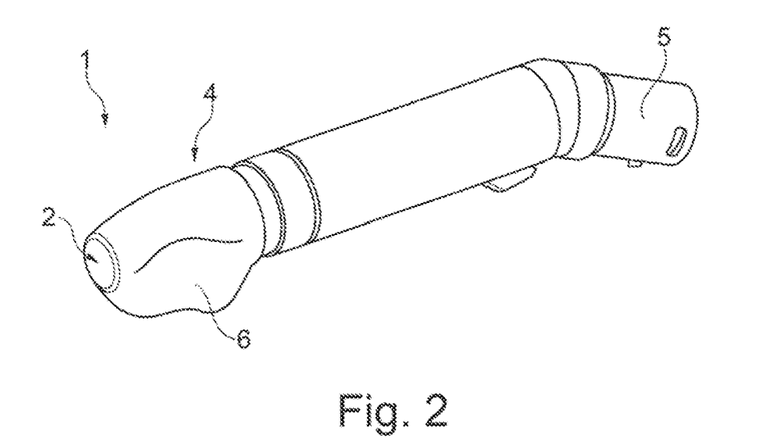
FIG. 2 shows a second embodiment of a surgical grip according to the invention with the actuation sleeve being provided with recessed grips, in a representation comparable to FIG. 1.

Referring to FIG. 1, it is noted that, although the activation unit 3 and the carrier sleeve 2 are concentrically surrounded by an actuation sleeve 4, the actuation sleeve 4 is present at a distal end of the surgical grip 1, an energy supply unit is adapted to be coupled to a proximal end. As shown in FIG. 2, an appropriate connecting piece 5 may include a longitudinal axis which is inclined relative to the longitudinal axis of the remaining surgical grip 1.

Figure 3:
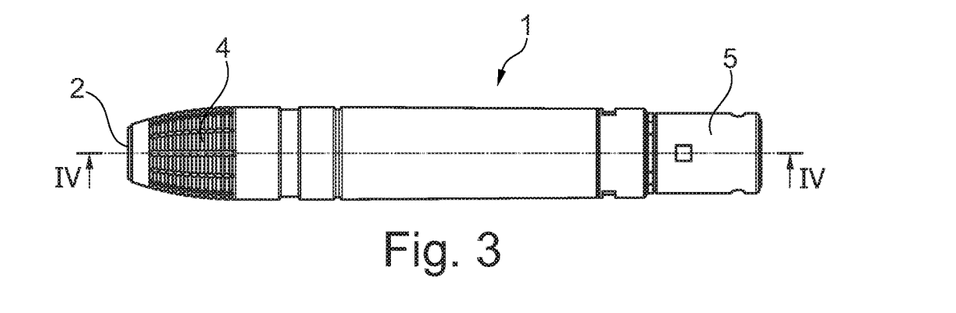
FIG. 3 shows a lateral view of the embodiment of FIG. 1.
Figure 4:
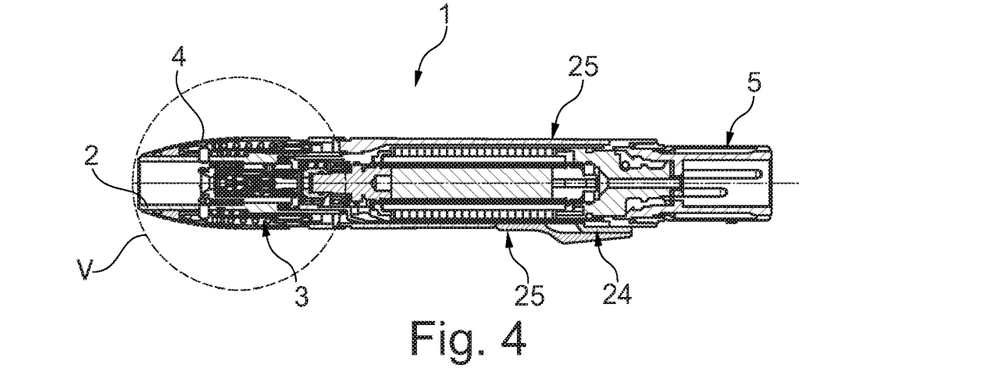
FIG. 4 shows a longitudinal section along the line IV across the embodiment of FIG. 3.

In the embodiment shown in FIG. 2, the actuation sleeve 4 includes at least one recessed grip 6. Here two recessed grips 6 are contained. While the surgical grip 1 shown in FIG. 1 is represented to be straight/not angled, the surgical grip 1 shown in FIG. 2 is thus designed to be angled. Such straight surgical grip 1 is also shown in FIGS. 3 and 4.

Figure 5:
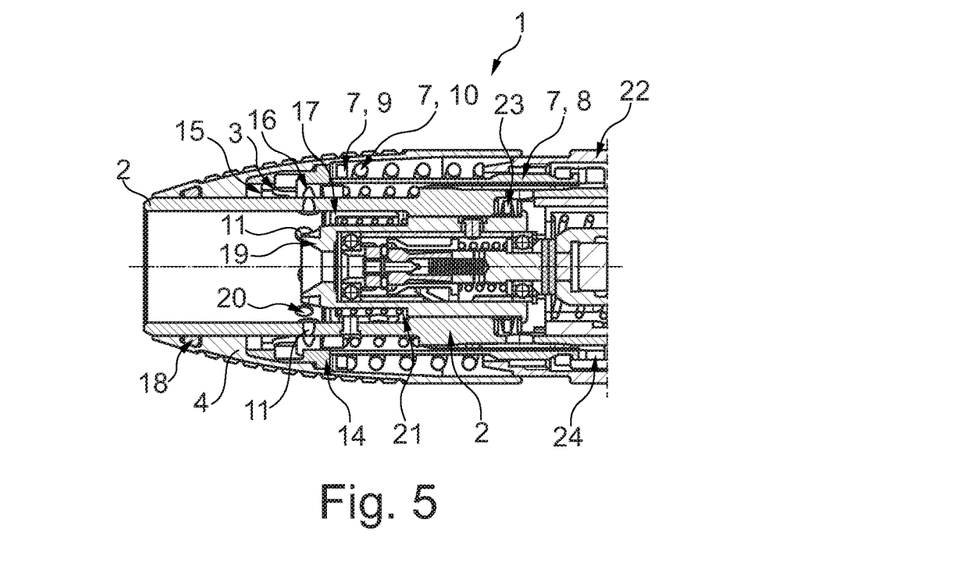
FIG. 5 shows a detailed representation of the area V of FIG. 4.
Figure 15:
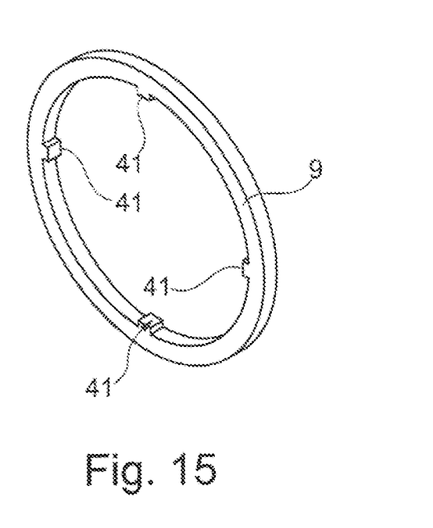
FIG. 15 shows a perspective view of a support ring inserted in a rotation securing unit.
Figure 16:
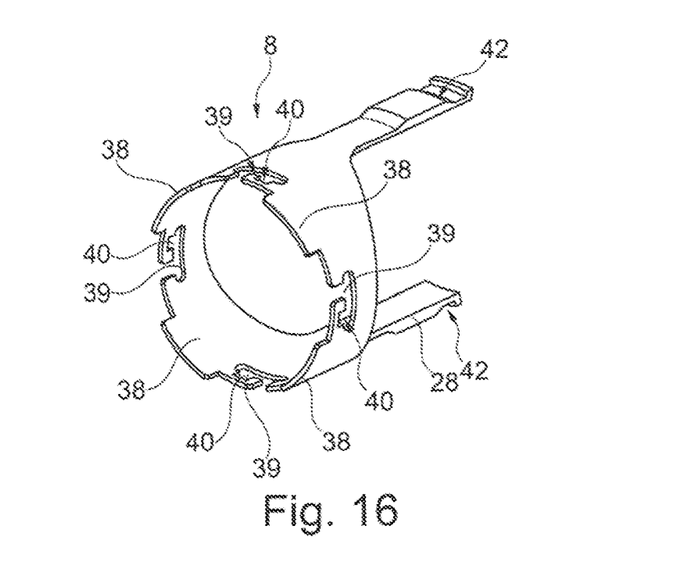
FIG. 16 shows a perspective view of a transmission sleeve inserted in a rotation securing unit.

Especially suited for the comprehension of the invention is further FIG. 5. There also a rotation securing unit 7 is shown. The rotation securing unit 7 comprises a transmission sleeve 8, a support ring 9 and a rotation securing spring/anti-rotation spring 10. With respect to the support ring 9 and the transmission sleeve 8, already now reference is made to FIGS. 15 and 16.

Referring to FIG. 5, it is outlined that the actuation sleeve 4 is the radially outermost component. Through openings 11 are present in a wall of the carrier sleeve 2 through which coupling components 12 (not shown in FIG. 5) (cf. e.g. FIGS. 8 and 9 in this respect) of the ball type 13 (cf. FIGS. 6 to 9) pass in order to couple and to retain a handpiece shaft not shown.

The activation unit 3 includes a stop sleeve 14 and a closing sleeve 15 separate therefrom. The closing sleeve 15 is arranged concentrically inside the stop sleeve 14 and includes such specific inner contour which becomes operatively correlated with the balls 13. On the proximal side of the closing sleeve 15, a pin rotation securing means 16 is provided.

A so-called tracing sleeve 17 is provided inside the carrier sleeve 2 so as to displace the coupling components 12 in due time out of the through openings 11.

In a circumferential notch on the inside of the actuation sleeve 4 an O-ring 18 is arranged.

Inside the carrier sleeve 2 also a tool coupling marked by the reference numeral 19 is visualized. In the area of the distal front-face end of the tool coupling 10 also the through openings 11 for realizing a ball attachment coupling 20 are provided. The carrier sleeve 2 may also be referred to as carrier, wherein the tracing sleeve 17 is disposed between the carrier sleeve 2 and the tool coupling 19. A compression spring 21 is also arranged between the tracing sleeve 17 and the tool coupling 19. At the proximal end of the actuation sleeve 4, an intermediate cover sleeve 22 is further located in a sealing manner. Said intermediate cover sleeve 22 is tightly connected, especially screwed, to the carrier sleeve 2. A tension spring 23 is mounted between the tool, coupling 19 and the carrier sleeve 2.

A latching sleeve 24 acts on the proximal end of the transmission sleeve 8. Said latching sleeve 24 may also be configured in the type of and referred to as a latching web. Radially outside of the latching sleeve 24 an actuator for an opening slide of the tool coupling 19 is provided. The actuator is provided with the reference numeral 25.

Referring to FIG. 4, it is further added that a separate outer housing 26 is inserted for defining a grip area to the proximal direction.

Figure 6:
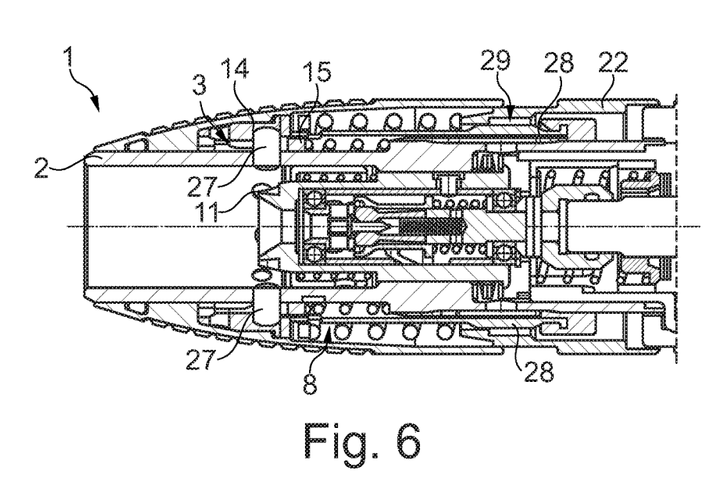
FIG. 6 shows a longitudinal section in the area of stop pins when the coupling is locked.
Figure 7:
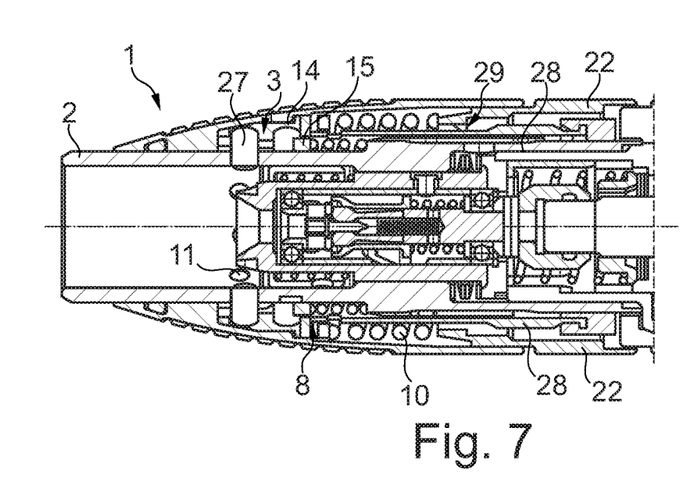
FIG. 7 shows a longitudinal section in the area of the stop pins when the coupling is opened.

In FIGS. 6 and 7, the activation unit 3 is shown with its stop sleeve 14 and its closing sleeve 15 in a locking position (FIG. 6) and, resp., an opening position (FIG. 7). The two operating states, viz. the locking position and the opening position, are defined by a stop at the stop pin 27.

Figure 8:
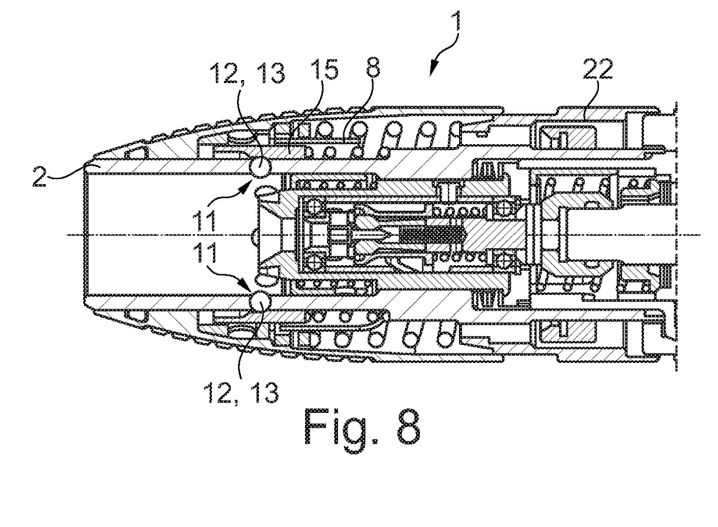
FIG. 8 shows a longitudinal section in the area of coupling components of the ball type, with a locked coupling of the surgical grip of FIG. 6.
Figure 9:
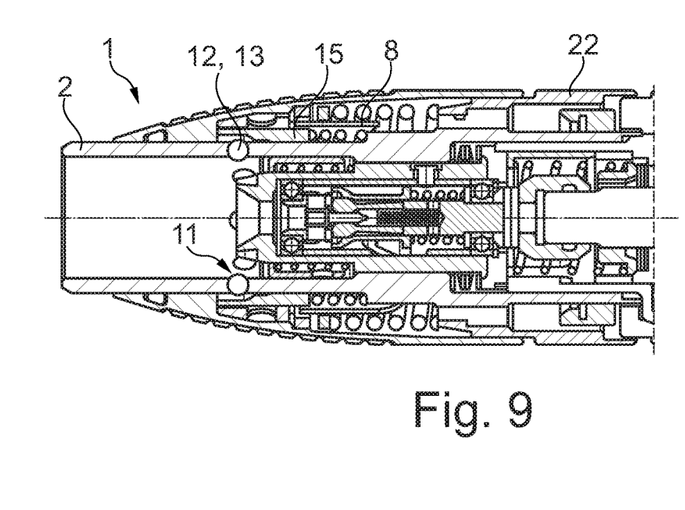
FIG. 9 shows a longitudinal section across the surgical handle of FIG. 7, wherein the section now is arranged in the area of the coupling components/balls again, when the coupling is opened.

In the locking position, a proximal part of the stop sleeve 14 abuts against the stop pin 27, whereas a distal part of the stop sleeve 14 abuts against the stop pin 27 in the opening position. Due to this fact, also axial displacement of the closing sleeve 15 is brought about, resulting in the corresponding positions as shown in FIGS. 8 and 9. While the balls 13 are blocked in the through opening 11 by the closing sleeve 15, viz. by the inner contour thereof, in the representation of FIG. 8 and thus the coupling is locked, in FIG. 9, viz. in the opening position, the balls 13 are released so that the coupling is opened.

The transmission sleeve 8 includes guiding arms 28 extending in an outwardly opening channel-type guiding groove 29 in the longitudinal/axial direction.

Figure 10:
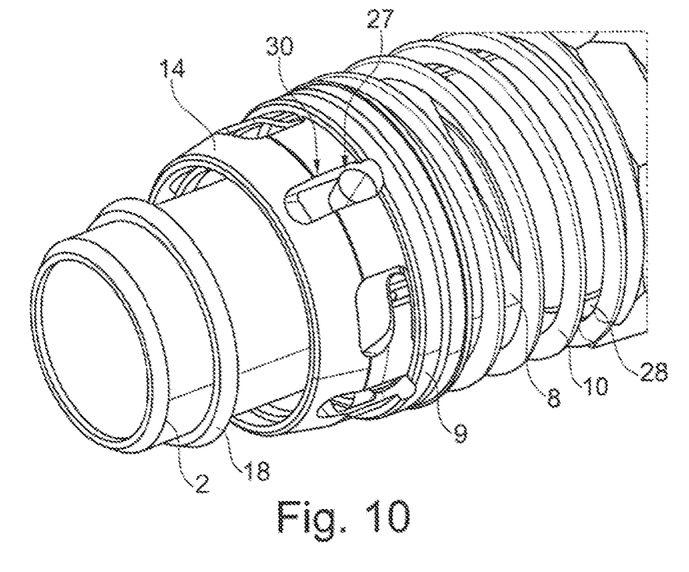
FIG. 10 shows the interior of the surgical grip in a perspective view without an actuation sleeve, when the coupling is locked.
Figure 11:
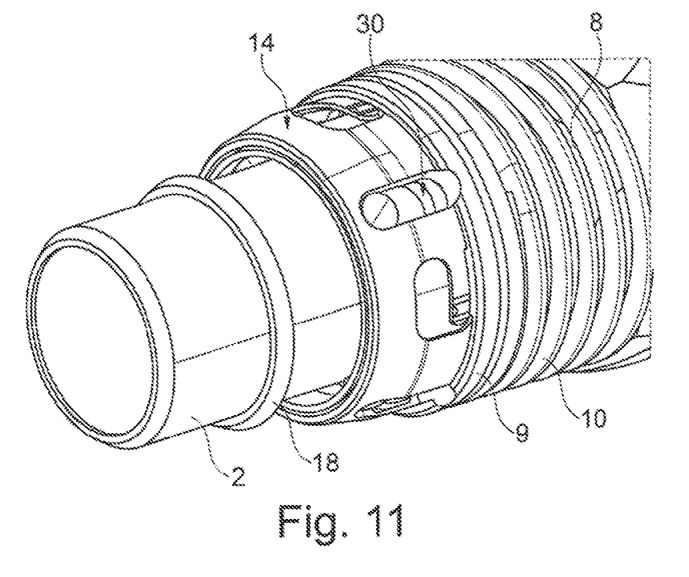
FIG. 11 shows a representation of the surgical grip without an actuation sleeve, when the coupling is opened.

In FIG. 10 the coupling is locked, whereas in FIG. 11 the coupling is opened such that the stop pin 27 is guided to be axially movable in a stop pin guiding groove 30 of the stop sleeve 14, or vice versa. In the locked position (FIG. 10) the stop pin 27 resides in the proximal end portion of the stop pin guiding groove 30, whereas in the distal end portion of the stop pin guiding groove 30 it resides in the opened coupling position. The rotation securing spring 10 is in pressing contact with the support ring 9.

Figure 12:
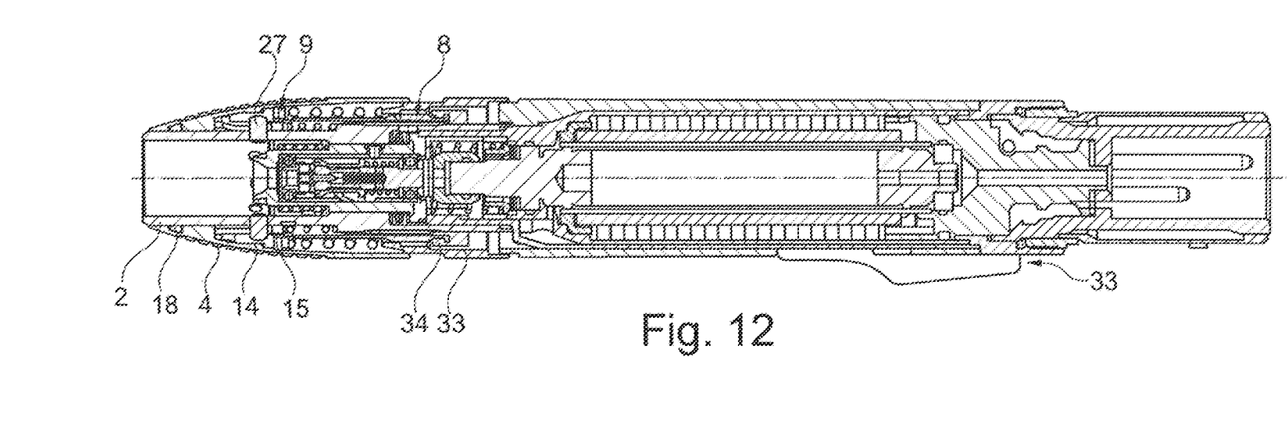
FIG. 12 shows an overall view of the surgical grip in the longitudinal section located in the area of the stop pins, when the coupling is locked and a latching web is retracted.
Figure 13:
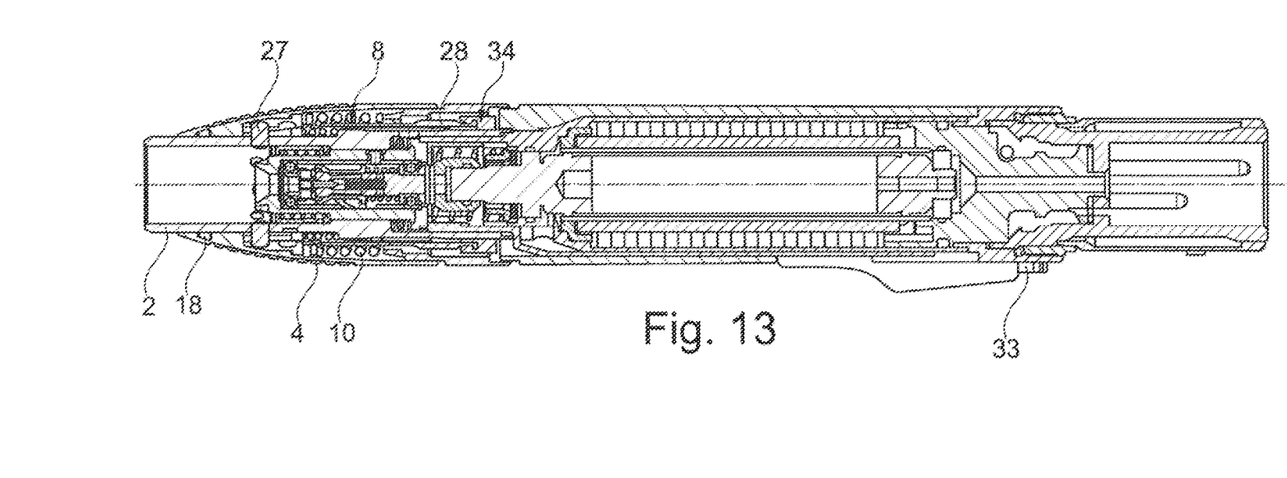
FIG. 13 shows an overall view of the surgical grip in the longitudinal section, with the sectional plane being located in the area of the stop pins and the coupling is opened, with the latching web thriller being extended.
Figure 14:
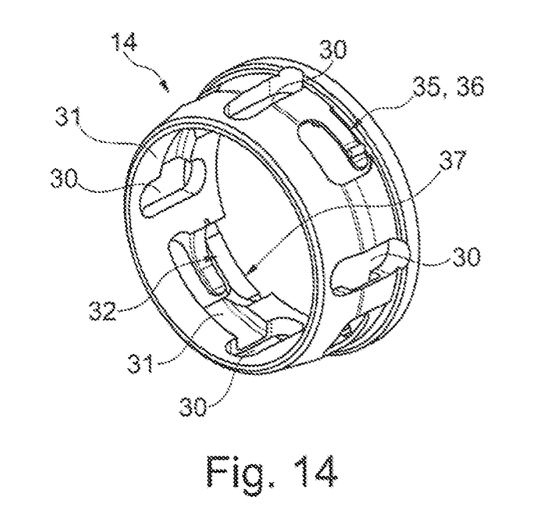
FIG. 14 shows a perspective view of the stop sleeve inserted in an activation unit.

The stop pin 27 is has only such length that it can also immerse into a radial release groove 31 shown in FIG. 14 which then is transformed to an orthogonally branching axial release groove 32. The stop pin 27 enters the two release grooves 31 and 32 only when this is desired by the service staff, namely when the support ring 9 is displaced with the transmission sleeve 8 against the rotation securing spring 10 actively, using a latching web 33 (cf. FIGS. 12 and 13), in the proximal direction.

Therefore, as is also clearly visible from FIG. 13, a connecting element 34 is used for axially fastening a proximal end of a guiding arm 28 of the transmission sleeve 8 to a distal end of the latching web 33. Form closure and/or force closure is used for attaching the two components to each other.

On the outside of the stop sleeve 14 a mount retaining tab 35 is formed in the way of a clip spring 36. Said clip spring 36, especially 2, 3, 4, 5 of said clip springs 36, are dimensioned/provided/adapted for getting, in non-positive and/or positive contact with the actuation sleeve 4.

At the proximal end of the stop sleeve 14, especially in the area of the proximal outlet of the axial release groove 32, rotation securing grooves 37 are present which are provided for interaction with rotation securing projections of the transmission sleeve 8. The rotation securing grooves 37 and the rotation securing projections 38 may as well be attached to the respective other component. The rotation securing groove 37 may also be referred to as rotation securing recess, whereas the rotation securing projection 38 may also be referred to as rotation securing tab.

It is further important that recesses 39 (see FIG. 16) kept available at the transmission sleeve 8, especially in the distal end portion, for a bayonet-type form closure having detent areas 40 for support lugs 41 to be introduced to the latter (see FIG. 15) are present on the inside of the support ring 9.

In the area of the proximal end of the guiding arms 28 (see FIG. 16) connecting element receiving notches 42 are provided.

Figure 17:
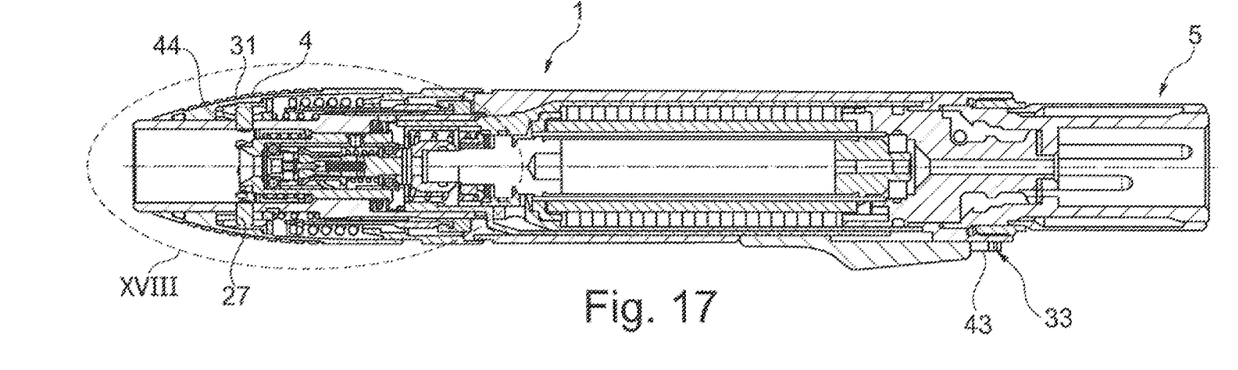
FIG. 17 shows an overall view of the surgical grip in the longitudinal section, with the sectional plane being located in the area of the stop pins, when the disassembly position is adopted.

In FIG. 17 tool application notches 43 are visualized at the latching web 33 and a bottom of the actuation sleeve 4 is provided with the reference numeral 44.

Figure 18:
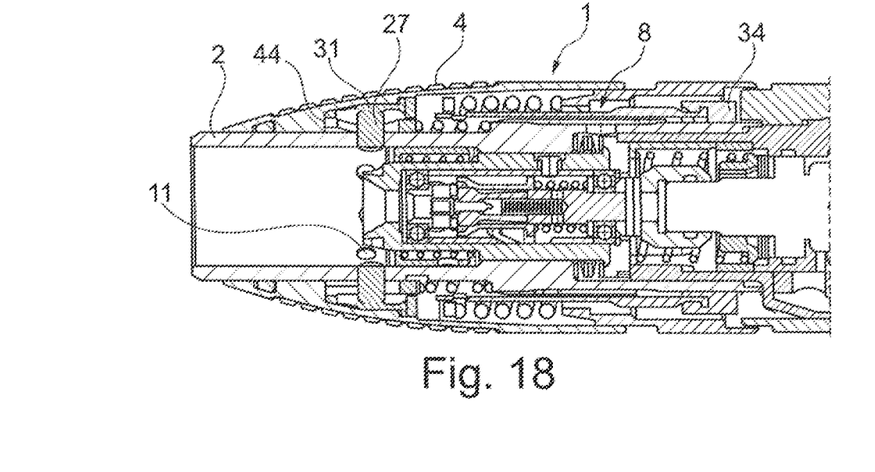
FIG. 18 shows an enlargement of the area XVIII of FIG. 17, wherein for disassembly the actuation sleeve is moved to the opening position of the coupling, then the latching web is fixed by a specific retaining tool, with the latching web including respective lateral notches, wherein the transmission sleeve is held at the rear/proximal position by the fixation of the latching web and then the actuation sleeve can be pushed forward until the radial release groove is provided level with the stop pins.
Figure 19:
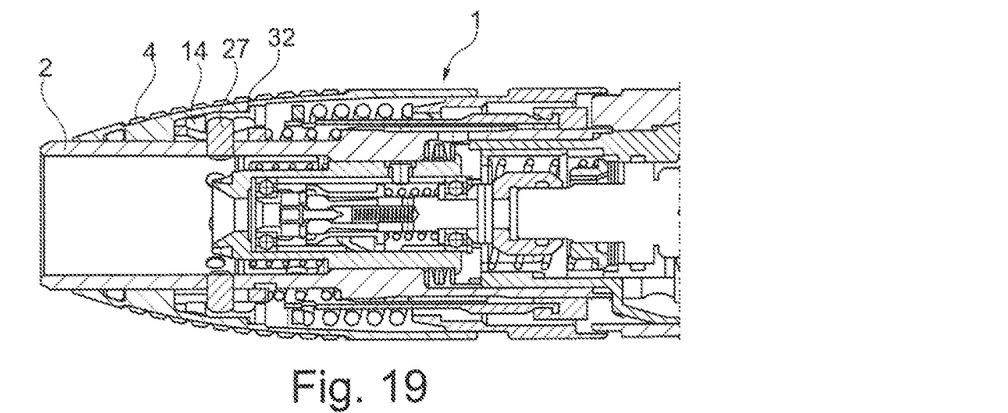
FIG. 19 shows a cutout representation of a longitudinal section of a surgical grip according to the invention, wherein the sectional plane is located in the area of the stop pins and an axial release groove is used for disassembly, wherein the rotation securing means of the transmission sleeve does no longer engage in the stop sleeve, which is why the actuation sleeve is rotatable anti-clockwise until the axial release groove of the stop sleeve is reached.
Figure 20:
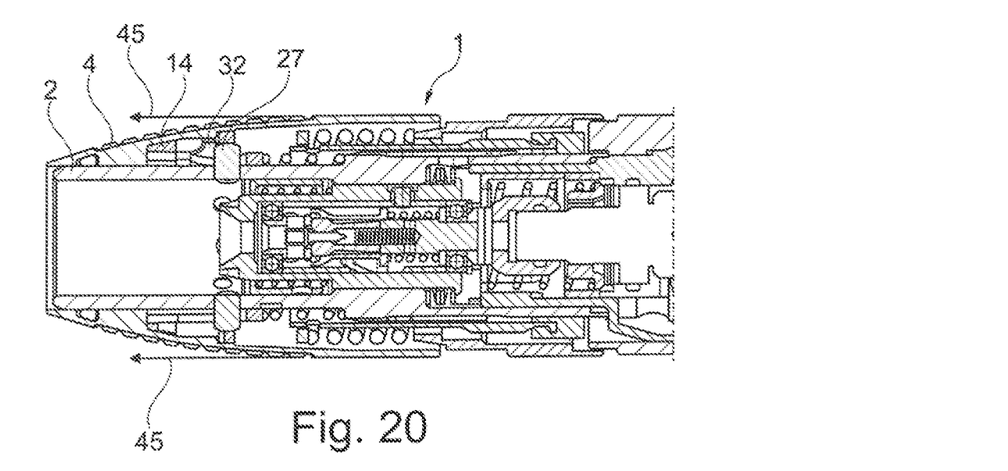
FIG. 20 shows a representation comparable to FIG. 19, with a final disassembly by removal being indicated by arrows, however, wherein in this position the actuation sleeve thus can be removed to the front, then the fixation of the latching web can be released and for repeated assembly no more fixation of the latching web is required, wherein further the actuation sleeve is pushed to the position of the axial release groove over the stop pins until the radial release groove is reached, and moreover the actuation sleeve is subsequently rotated clockwise until the stop pins are adjacent to the wall of the guiding groove, wherein by the spring, force the transmission sleeve is automatically locked in the groove for rotation securing.

In FIG. 18 entering of the stop pin 27 into the radial release groove 31 is evident, just as in FIG. 17, although there a slightly smaller scale is applied. The further movement into the axial release groove 32 and then the exiting from the stop sleeve 14 is evident in FIGS. 19 and 20. The direction of removal is visualized by the arrow 45.

Figure 21:
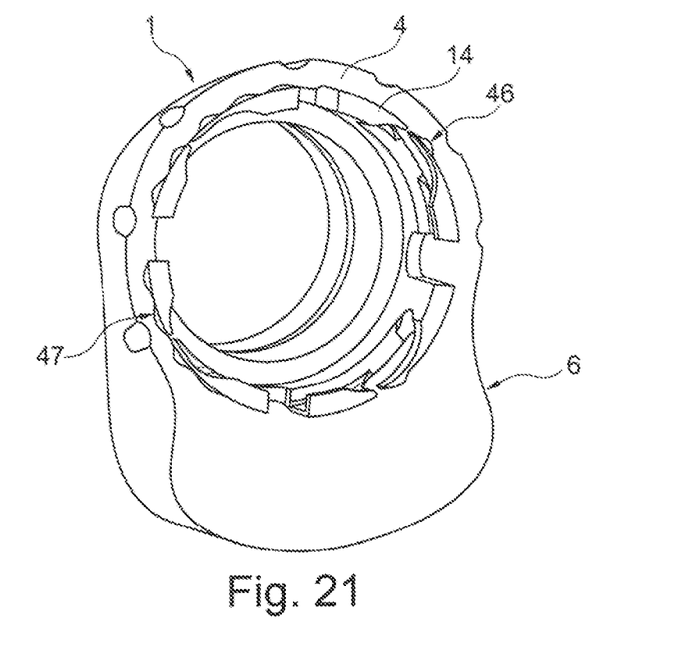
FIG. 21 shows an embodiment different from the one of the preceding figures and configurations in which the locking lugs and detent contours (alternately) engage in each other at the stop sleeve and, resp., the actuation sleeve.
Figure 22:
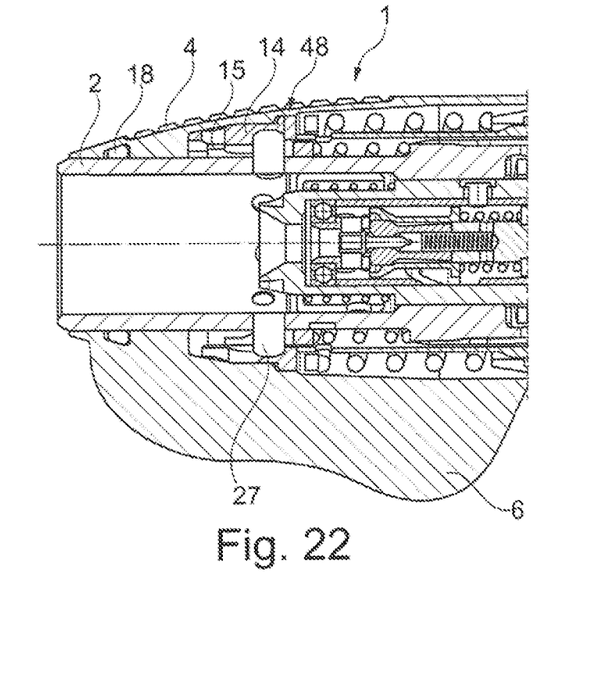
FIG. 22 shows a mode of representation comparable to FIGS. 19 and 20 making use of an angled handpiece and an actuation sleeve having recessed grips (similarly to FIG. 2), wherein the longitudinal section is located in the area of the stop pins and the clip springs of the stop sleeve are provided with locking lugs, with the latter engaging in corresponding detent contours of the actuation sleeve, and further the stop sleeve in this configuration is fixed in the axial direction by means of a circlip.

A surgical grip 1 different from the afore-discussed surgical grip embodiments is illustrated in FIGS. 21 and 22. It is a particular modification in this case that detent lugs 46 positively and/or non-positively engaging in preferably diametrically opposed detent contours 47 of die actuation sleeve 4 are present at the stop sleeve 14. The axial securing of the stop sleeve 14 is realized by a circlip 48.

The invention claimed is:

1. A surgical grip for receiving a handpiece shaft for conjoint rotation therewith and/or for receiving a medical tool in such a way as to transmit torque, comprising a carrier sleeve on which at least one coupling component provided for coupling the handpiece shaft is attached such that the at least one coupling component can be brought to a coupled position and to an uncoupled position in an operating state in which disassembly of the surgical grip is excluded, wherein the at least one coupling component can be brought into contact with an activation unit which is arranged between the carrier sleeve and an outer actuation sleeve by actuation of which the at least one coupling component can be coupled and/or uncoupled via the activation unit, wherein the surgical grip defines a longitudinal axis that extends through a center of the surgical grip, and wherein the surgical grip comprises a rotation securing unit present inside the actuation sleeve which acts on the activation unit in a spring-biased manner in the operating state such that the activation unit is held secure against rotation relative to the carrier sleeve,
wherein the activation unit includes a closing sleeve and a stop sleeve separate therefrom and radially encompassing said closing sleeve, and
wherein the stop sleeve is connected to the actuation sleeve in an axially fixed manner with respect to the longitudinal axis and is adapted to be radially adjusted with respect to the longitudinal axis.

2. The surgical grip according to claim 1, wherein the actuation sleeve is configured to be displaced in a disassembly state different from the operating state to a position enabling rotation of the activation unit.

3. The surgical grip according to claim 1, wherein the rotation securing unit is configured to be rotationally fixed but axially movable at the carrier sleeve.

4. A surgical grip for receiving a handpiece shaft for conjoint rotation therewith and/or for receiving a medical tool in such a way as to transmit torque, comprising a carrier sleeve on which at least one coupling component provided for coupling the handpiece shaft is attached such that the at least one coupling component can be brought to a coupled position and to an uncoupled position in an operating state in which disassembly of the surgical grip is excluded, wherein the at least one coupling component can be brought into contact with an activation unit which is arranged between the carrier sleeve and an outer actuation sleeve by actuation of which the at least one coupling component can be coupled and/or uncoupled via the activation unit, wherein the surgical grip comprises a rotation securing unit present inside the actuation sleeve which acts on the activation unit in a spring-biased manner in the operating state such that the activation unit is held secure against rotation relative to the carrier sleeve,
wherein the activation unit includes a closing sleeve and a stop sleeve separate therefrom and radially encompassing said closing sleeve,
wherein the rotation securing unit is forced into contact with the activation unit via a rotation securing spring which bears against a portion or component fixed to the carrier sleeve, and
wherein front-face rotation securing tabs of the rotation securing unit in the operating state engage in rotation securing recesses which are arranged in the activation unit and wherein by axially displacing the rotation securing unit against a biasing force of the rotation securing spring, the stop sleeve is released and in this way the actuation sleeve is enabled to rotate into the disassembly position.

5. The surgical grip according to claim 4, wherein the actuation sleeve is configured to be displaced in a disassembly state different from the operating state to a position enabling rotation of the activation unit.

6. The surgical grip according to claim 4, wherein the rotation securing unit is configured to be rotationally fixed but axially movable at the carrier sleeve.

* * * * *